(12) United States Patent
Raineau et al.

(10) Patent No.: US 9,993,400 B2
(45) Date of Patent: *Jun. 12, 2018

(54) COSMETIC COMPOSITION COMPRISING AN ALKYL PHOSPHATE AND A FATTY ALKYL ETHER OF POLYETHYLENE GLYCOL, PROCESSES THEREFOR AND USES THEREOF

(71) Applicant: L'OREAL, Paris (FR)

(72) Inventors: Olivier Raineau, Paris (FR); Isabelle Jacquier, Chevilly Larue (FR)

(73) Assignee: L'OREAL, Paris (FR)

(*) Notice: Subject to any disclaimer, the term of this patent is extended or adjusted under 35 U.S.C. 154(b) by 0 days. days.

This patent is subject to a terminal disclaimer.

(21) Appl. No.: 15/460,671

(22) Filed: Mar. 16, 2017

(65) Prior Publication Data

US 2017/0181938 A1    Jun. 29, 2017

Related U.S. Application Data

(63) Continuation of application No. 11/934,889, filed on Nov. 5, 2007, now Pat. No. 9,687,426.

(60) Provisional application No. 60/868,749, filed on Dec. 6, 2006.

(30) Foreign Application Priority Data

Nov. 10, 2006   (FR) ...................... 06 54827

(51) Int. Cl.
| A61K 8/55 | (2006.01) |
| A61K 8/34 | (2006.01) |
| A61K 8/92 | (2006.01) |
| A61Q 1/10 | (2006.01) |
| A61K 8/06 | (2006.01) |
| A61K 8/19 | (2006.01) |
| A61K 8/39 | (2006.01) |
| A61K 8/86 | (2006.01) |

(52) U.S. Cl.
CPC ............... *A61K 8/06* (2013.01); *A61K 8/19* (2013.01); *A61K 8/345* (2013.01); *A61K 8/39* (2013.01); *A61K 8/55* (2013.01); *A61K 8/86* (2013.01); *A61K 8/92* (2013.01); *A61Q 1/10* (2013.01); *A61K 2800/43* (2013.01); *A61K 2800/596* (2013.01)

(58) Field of Classification Search
None
See application file for complete search history.

(56) References Cited

U.S. PATENT DOCUMENTS

| 4,460,571 | A   |   | 7/1984  | Gomez                      |
|-----------|-----|---|---------|----------------------------|
| 4,828,826 | A   |   | 5/1989  | Franz                      |
| 4,917,891 | A   |   | 4/1990  | Kaufmann et al.            |
| 5,599,547 | A   | * | 2/1997  | Bartholomey ..... A61K 8/375 |
|           |     |   |         | 424/401                    |
| 5,607,980 | A   |   | 3/1997  | McAtee et al.              |
| 6,039,935 | A   |   | 3/2000  | Mohammadi                  |
| 6,156,804 | A   |   | 12/2000 | Chevalier et al.           |
| 6,302,920 | B1  | * | 10/2001 | Lorenz ............... A61K 8/86 |
|           |     |   |         | 132/208                    |
| 6,375,941 | B1  | * | 4/2002  | Piot ................. A61K 8/87 |
|           |     |   |         | 424/70.1                   |
| 6,468,550 | B1  |   | 10/2002 | Remy                       |
| 6,548,074 | B1  |   | 4/2003  | Mohammadi                  |

FOREIGN PATENT DOCUMENTS

| EP | 1 083 184      |   | 3/2001  |
|----|----------------|---|---------|
| EP | 1 529 513      |   | 5/2005  |
| WO | 01/13863       |   | 3/2001  |
| WO | 02/098379      |   | 12/2002 |
| WO | 2005/039514    |   | 5/2005  |
| WO | WO2005039515   | * | 5/2005  |
| WO | 2008/015272    |   | 2/2008  |

OTHER PUBLICATIONS

Loden et al, Dry Skin and Moisturizers, Chemistry and Function, CRC Press, 2000, pp. 1-3.
Michlun, Skin Care and Cosmetic Ingredients Dictionary, Milady Publishing, 1994, pp. 1-3.
SciFinder Amphisol A—retrieved online on Sep. 3, 2015.

* cited by examiner

*Primary Examiner* — Jennifer A Berrios
(74) *Attorney, Agent, or Firm* — Oblon, McClelland, Maier & Neustadt, L.L.P.

(57) ABSTRACT

A mascara composition including water; an emulsifying system of at least one $C_{16}$-$C_{18}$ alkyl phosphate and at least one $C_{16}$-$C_{22}$ fatty alkyl ether of polyethylene glycol, the ether with 1 to 19 ethylene glycol units and having an HLB<8 at 25° C.; at least one pigment having a color; and at least one wax; wherein the emulsification system inhibits aggregation of the pigment in the mascara composition such that the color of the pigment is not inhibited, and wherein the mascara composition has a viscosity ranging from 1 to 60 Pa·s.

8 Claims, No Drawings

COSMETIC COMPOSITION COMPRISING AN ALKYL PHOSPHATE AND A FATTY ALKYL ETHER OF POLYETHYLENE GLYCOL, PROCESSES THEREFOR AND USES THEREOF

REFERENCE TO PRIOR APPLICATIONS

This application is a continuation of U.S. application Ser. No. 11/934,889 filed Nov. 5, 2007, which is incorporated herein by reference and allowed, and claims the benefit of U.S. provisional application 60/868,749 filed Dec. 6, 2006, and French patent application 06 54827 filed Nov. 10, 2006, both incorporated herein by reference.

FIELD OF THE INVENTION

The present patent application relates to the field of making up or caring for keratin fibres such as the eyelashes or the eyebrows, and more particularly relates to eyelash coating compositions, or mascaras.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

Eyelash coating compositions such as mascaras are generally makeup compositions, compositions to be applied over a makeup (also known as top coats), or cosmetic eyelash care compositions.

Mascaras are especially prepared according to two types of formulation: water-based mascaras known as cream mascaras, in the form of a dispersion of waxes in water; mascaras that are anhydrous or that have a low water content, known as waterproof mascaras, in the form of dispersions of waxes in organic solvents.

The present patent application more specifically concerns water-based mascaras.

Application of mascara makes it possible to increase the volume of the eyelashes and consequently to increase the intensity of the gaze. Many thickening or volumizing mascaras exist for doing this, the principle of which consists in depositing the maximum amount of material onto the eyelashes so as to obtain a volumizing (or charging) effect.

It is in particular by means of the amount of solid particles (especially waxes, which make it possible to structure the composition) that the application specificities desired for the compositions can be adjusted, for instance their fluidity or consistency, and also their thickening power (also known as the charging power or makeup power).

These solid particles are dispersed in the cream mascara by means of a surfactant system.

Among the standard emulsifiers or emulsifying systems, there are cetyl phosphate, but the use of cetyl phosphate alone leads to aggregation of the pigments and also to coarse dispersion of the waxes; this frequently results in a "grey" rather than a black mascara;

emulsifying systems based on Steareth-20 and Steareth-2, but the use of these systems leads to very fluid mascaras whose consistency is unsatisfactory for a volumizing mascara;

emulsifying systems based on triethanolamine stearate.

One problem addressed by the present patent application is a mascara in which not only the waxes but also the pigments are dispersed uniformly, the mascara having a texture that is thick enough to obtain a charging, volumizing deposit on the eyelashes, and having a satisfactory consistency allowing easy application to the eyelashes and smooth, uniform deposition.

SUMMARY OF THE INVENTION

The inventors of the present patent application have, surprisingly and unexpectedly, solved this problem by providing an emulsifying system containing at least one $C_{10}$-$C_{30}$ alkyl phosphate and at least one $C_8$-$C_{24}$ fatty alkyl ether of polyethylene glycol, the ether comprising from 1 to 19 ethylene glycol units and having an HLB<8 at 25° C.

The inventors of the present patent application have observed that the emulsifying system defined in the present patent application allows good dispersion of pigments and/or waxes, this dispersion being of the quality of those obtained with emulsifying systems based on triethanolamine stearate. This composition makes it possible to obtain a charging makeup for keratin fibres and a smooth, uniform deposit on the fibres.

DETAILED DESCRIPTION OF THE PREFERRED EMBODIMENTS

The composition according to the invention advantageously has a viscosity generally ranging from 1 to 60 Pa·s, preferably from 1.5 to 50 Pa·s, better still from 2 to 40 Pa·s and even better still from 3 to 30 Pa·s.

The viscosity of the composition is measured at 25° C. using a Rheomat 180 viscometer (from the company Lamy) equipped with an MS-R1, MS-R2, MS-R3, MS-R4 or MS-R5 spindle chosen as a function of the consistency of the composition, rotating at a spin speed of 200 rpm. The measurement is taken after 10 minutes of rotation.

A first subject of the present patent application is a composition for coating keratin fibres, comprising an aqueous phase and an emulsifying system, such that the emulsifying system comprises:

at least one $C_{10}$-$C_{30}$ alkyl phosphate and at least one $C_8$-$C_{24}$ fatty alkyl ether of polyethylene glycol, the ether comprising from 1 to 19 ethylene glycol units and having an HLB<8 at 25° C.

The HLB (hydrophilic-lipophilic balance) in the Griffin sense is defined in J. Soc. Cos. Chem. 1954 (volume 5), pages 249-256.

A second subject of the present patent application is a process for making up or for non-therapeutically caring for keratin fibres, comprising the application to the keratin fibres of the composition according to the present patent application.

A third subject of the present patent application concerns the uses of the composition according to the present patent application, in particular the use of this composition for obtaining uniform and/or volumizing makeup on the eyelashes.

Other characteristics, properties and advantages of the present invention will emerge more clearly on reading the description and the examples that follow.

Emulsifying System

The alkyl phosphate(s) that may be used in the compositions according to the present patent application is (are) preferably chosen from $C_{14}$-$C_{24}$ and preferably $C_{16}$-$C_{18}$ alkyl phosphates, and mixtures thereof. Even more preferably, they are chosen from cetyl phosphate, stearyl phosphate and cetearyl phosphate. The alkyl phosphate is particularly cetyl phosphate, for example sold under the names Amphisol K (Roche), Amphisol A (Roche), Arlatone MAP (Uniqema) and Crodafos MCA (Croda).

The content of alkyl phosphate(s) is not limited and preferably generally ranges from 0.1% to 20% by weight and more preferably from 0.5% to 12% by weight relative to the total weight of the composition.

The $C_8$-$C_{24}$ fatty alkyl ether(s) of polyethylene glycol comprising from 1 to 19 ethylene glycol units and having an HLB<8 at 25° C., which may be used in the compositions according to the present patent application, is (are) preferably chosen from $C_{16}$-$C_{22}$ fatty alkyl ethers of polyethylene glycol comprising from 1 to 19 ethylene glycol units.

The fatty alkyl ether of polyethylene glycol is particularly the compound bearing the INCI name Steareth-2 (polyethylene glycol (2) stearyl ether) with an HLB equal to 5, this product being sold, for example, under the names Brij 72 (Uniqema) and Volpo S2 (Croda).

The content of $C_8$-$C_{24}$ fatty alkyl ether of polyethylene glycol comprising from 1 to 19 ethylene glycol units and of HLB<8 at 25° C. preferably generally ranges from 0.1% to 20% by weight and more preferably from 0.5% to 10% by weight relative to the total weight of the composition.

According to one embodiment, the emulsifying system containing the combination of $C_{10}$-$C_{30}$ alkyl phosphate and of $C_8$-$C_{24}$ fatty alkyl ether of polyethylene glycol, the ether comprising from 1 to 19 ethylene glycol units and having an HLB<8 at 25° C., constitutes the main surfactant system of the composition.

The term "main surfactant system" means a system which, in its absence, does not lead to the formation of a stable composition.

The term "stable" means a composition which, after having been placed in an oven at 45° C. for two months, does not have, after returning to room temperature, any grains that are perceptible to the touch, when a thin coat of the composition is sheared between the fingers.

According to one particular embodiment, the emulsifying system containing the combination of $C_{10}$-$C_{30}$ alkyl phosphate and of $C_8$-$C_{24}$ fatty alkyl ether of polyethylene glycol, the ether comprising from 1 to 19 ethylene glycol units and having an HLB<8 at 25° C., constitutes the sole surfactant system of the composition.

The tem' "sole" means that any possible additional surfactant system is present in a content not exceeding 1% and preferably not exceeding 0.5%. More preferably, the term "sole" denotes a total absence of any other surfactant system.

According to one variant, the cosmetic composition according to the present patent application comprises less than 1% and preferably less than 0.5% by weight of triethanolamine, and better still is free of triethanolamine.

According to one preferred variant, the cosmetic composition according to the present patent application comprises less than 1% and preferably less than 0.5% by weight of triethanolamine stearate, and better still is free of triethanolamine stearate.

The composition according to the invention obviously comprises a physiologically acceptable medium. For the purposes of the present patent application, the term "physiologically acceptable compound or medium" means a compound or medium whose use is compatible with application to the eyelashes.

Aqueous Phase

The composition according to the invention comprises an aqueous phase, which may form the continuous phase of the composition.

The term "composition with a continuous aqueous phase" means that the composition has a conductivity, measured at 25° C., of greater than 23 µS/cm (microSiemens/cm), the conductivity being measured, for example, using an MPC227 conductimeter from Mettler Toledo and an Inlab730 conductivity measuring cell. The measuring cell is immersed in the composition so as to remove any air bubbles liable to form between the two electrodes of the cell. The conductivity reading is taken once the conductimeter value has stabilized. A mean is determined over at least three successive measurements.

The aqueous phase comprises water and/or at least one water-soluble solvent.

In the present invention, the term "water-soluble solvent" denotes a compound that is liquid at room temperature and water-miscible (miscibility in water of greater than 50% by weight at 25° C. and atmospheric pressure).

The water-soluble solvents that may be used in the compositions according to the invention may also be volatile.

Among the water-soluble solvents that may be used in the compositions according to the invention, mention may be made especially of lower monoalcohols containing from 1 to 5 carbon atoms, such as ethanol and isopropanol, glycols containing from 2 to 8 carbon atoms, such as ethylene glycol, propylene glycol, 1,3-butylene glycol and dipropylene glycol.

The aqueous phase (water and optionally the water-miscible solvent) is generally present in the composition according to the present patent application in a content generally ranging from 1% to 95% by weight, preferably generally ranging from 3% to 80% by weight and preferentially generally ranging from 5% to 60% by weight relative to the total weight of the composition.

The emulsifying system may also contain at least one additional surfactant, other than the $C_{10}$-$C_{30}$ alkyl phosphates and the fatty alkyl ether of polyethylene glycol as defined above, appropriately chosen so as to obtain a wax-in-water or oil-in-water emulsion.

According to the present invention, the additional surfactant is not a surfactant system as defined above, given that this additional surfactant alone cannot lead to the formation of a stable composition, as defined above.

In particular, an emulsifier having at 25° C. an HLB (hydrophilic-lipophilic balance), in the Griffin sense, of greater than or equal to 8 may be used.

These additional surfactants may be chosen from nonionic, anionic, cationic and amphoteric surfactants or emulsifying surfactants. Reference may be made to Kirk-Othmer's "Encyclopedia of Chemical Technology", volume 22, pp. 333-432, 3rd edition, 1979, Wiley, for the definition of the properties and (emulsifying) functions of surfactants, in particular pp. 347-377 of this reference, for anionic, amphoteric and nonionic surfactants.

These additional surfactants may be preferentially chosen from:

a) nonionic surfactants with an HLB of greater than or equal to 8 at 25° C., used alone or as a mixture; mention may be made especially of:

oxyethylenated and/or oxypropylenated ethers (which may comprise from 1 to 150 oxyethylene and/or oxypropylene groups) of glycerol;

oxyethylenated and/or oxypropylenated ethers (which may comprise from 20 to 1000 oxyethylene and/or oxypropylene groups) of fatty alcohols (especially of $C_8$-$C_{24}$ and preferably $C_{12}$-$C_{18}$ alcohol), such as oxyethylenated stearyl alcohol ether containing 20 oxyethylene groups (CTFA name Steareth-20) such as Brij 78 sold by the company Uniqema, oxyethylenated cetearyl alcohol ether containing 30 oxyethylene groups (CTFA name Ceteareth-30) and the oxyethylenated ether of the mixture of $C_{12}$-$C_{15}$ fatty alcohols comprising 7 oxyethylene groups (CTFA name C12-15 Pareth-7) sold under the name Neodol 25-7® by Shell Chemicals;

fatty acid esters (especially of a $C_8$-$C_{24}$ and preferably $C_{16}$-$C_{22}$ acid) of polyethylene glycol (which may comprise from 1 to 150 ethylene glycol units), such as PEG-50 stearate and PEG-40 monostearate sold under the name Myrj 52P® by the company ICI Uniqema;

fatty acid esters (especially of a $C_8$-$C_{24}$ and preferably $C_{16}$-$C_{22}$ acid) of oxyethylenated and/or oxypropylenated glyceryl ethers (which may comprise from 1 to 150 oxyethylene and/or oxypropylene groups), for instance PEG-200 glyceryl monostearate sold under the name Simulsol 220 TM® by the company SEPPIC; glyceryl stearate polyethoxylated with 30 ethylene oxide groups, for instance the product Tagat S® sold by the company Goldschmidt, glyceryl oleate polyethoxylated with 30 ethylene oxide groups, for instance the product Tagat O® sold by the company Goldschmidt, glyceryl cocoate polyethoxylated with 30 ethylene oxide groups, for instance the product Varionic LI 13® sold by the company Sherex, glyceryl isostearate polyethoxylated with 30 ethylene oxide groups, for instance the product Tagat L® sold by the company Goldschmidt, and glyceryl laurate polyethoxylated with 30 ethylene oxide groups, for instance the product Tagat I® from the company Goldschmidt;

fatty acid esters (especially of a $C_8$-$C_{24}$ and preferably $C_{16}$-$C_{22}$ acid) of oxyethylenated and/or oxypropylenated sorbitol ethers (which may comprise from 1 to 150 oxyethylene and/or oxypropylene groups), for instance polysorbate 60 sold under the name Tween 60® by the company Uniqema;

dimethicone copolyol, such as the product sold under the name Q2-5220® by the company Dow Corning;

dimethicone copolyol benzoate (Finsolv SLB 101® and 201® by the company Finetex);

copolymers of propylene oxide and of ethylene oxide, also known as EO/PO polycondensates;

and mixtures thereof.

The EO/PO polycondensates are more particularly copolymers consisting of polyethylene glycol and polypropylene glycol blocks, for instance polyethylene glycol/polypropylene glycol/polyethylene glycol triblock polycondensates. These triblock polycondensates have, for example, the following chemical structure:

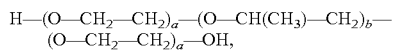

in which formula a generally ranges from 2 to 120 and b generally ranges from 1 to 100.

The EO/PO polycondensate preferably has a weight-average molecular weight generally ranging from 1000 to 15 000 and better still generally ranging from 2000 to 13 000. Advantageously, the EO/PO polycondensate has a cloud point, at 10 g/l in distilled water, of greater than or equal to 20° C. and preferably greater than or equal to 60° C. The cloud point is measured according to ISO standard 1065. As EO/PO polycondensates that may be used according to the invention, mention may be made of the polyethylene glycol/polypropylene glycol/polyethylene glycol triblock polycondensates sold under the name Synperonic®, for instance Synperonic PE/L44® and Synperonic PE/F127®, by the company ICI.

b) nonionic surfactants with an HLB of less than 8 at 25° C., optionally combined with one or more nonionic surfactants with an HLB of greater than 8 at 25° C., such as those mentioned above, such as:

saccharide esters and ethers, such as sucrose stearate, sucrose cocoate and sorbitan stearate, and mixtures thereof, for instance Arlatone 2121® sold by the company ICI;

fatty acid esters (especially of a $C_8$-$C_{24}$ and preferably $C_{16}$-$C_{22}$ acid) of polyols, especially of glycerol or of sorbitol, such as glyceryl stearate, glyceryl stearate such as the product sold under the name Tegin M® by the company Goldschmidt, glyceryl laurate such as the product sold under the name Imwitor 312® by the company Hüls, polyglyceryl-2 stearate, sorbitan tristearate or glyceryl ricinoleate;

the mixture of cyclomethicone/dimethicone copolyol sold under the name of Q2-3225C® by the company Dow Corning, c) anionic surfactants such as:

$C_{16}$-$C_{30}$ fatty acid salts, especially those derived from amines, for instance triethanolamine stearate and/or 2-amino-2-methyl-1,3-propanediol stearate; but preferably, the composition according to the present patent application does not contain any triethanolamine stearate;

polyoxyethylenated fatty acid salts, especially those derived from amines or alkali metal salts, and mixtures thereof;

alkyl ether sulfates, such as sodium lauryl ether sulfate; isethionates;

acylglutamates such as Disodium hydrogenated tallow glutamate (Amisoft HS-21 R® sold by the company Ajinomoto), and mixtures thereof.

The composition in accordance with the invention may also contain one or more amphoteric surfactants, for instance N-acylamino acids such as N-alkylaminoacetates and disodium cocoamphodiacetate, and amine oxides such as stearamine oxide, or alternatively silicone surfactants, for instance dimethicone copolyol phosphates such as the product sold under the name Pecosil PS 100® by the company Phoenix Chemical.

According to one particular embodiment, the composition comprises an additional surfactant of HLB>8 at 25° C., preferably a $C_8$-$C_{24}$ fatty alkyl ether of polyethylene glycol, the ether comprising from 20 to 1000 ethylene glycol units. The ether may be present in a content generally ranging from 0.1% to 10% by weight and preferably 0.2% to 8% by weight relative to the total weight of the composition.

Mention may be made in particular of oxyethylenated stearyl alcohol ether containing 20 oxyethylene groups (CTFA name: Steareth-20).

According to one preferred embodiment, the composition also comprises a co-surfactant chosen from fatty alcohols, preferably containing from 10 to 30 carbon atoms. The expression "fatty alcohol containing from 10 to 30 carbon atoms" means any saturated or unsaturated, branched or unbranched pure fatty alcohol containing from 10 to 30 carbon atoms.

A fatty alcohol containing from 10 to 26 carbon atoms, better still from 10 to 24 carbon atoms and even better still from 14 to 22 carbon atoms is preferably used.

As fatty alcohols that may be used in the composition, mention may be made especially of lauryl alcohol, myristyl alcohol, cetyl alcohol, stearyl alcohol, oleyl alcohol, cetearyl alcohol (mixture of cetyl alcohol and stearyl alcohol), behenyl alcohol and erucyl alcohol, and mixtures thereof. Cetyl alcohol is preferably used.

Such fatty alcohols are especially sold under the name Nafol by the company Sasol.

The fatty alcohol may be present in a content generally ranging from 0.2% to 20% by weight and preferably from 0.3% to 10% by weight relative to the total weight of the composition.

According to one embodiment, the composition according to the invention comprises, as emulsifying system, the following combination:
- at least one $C_{10}$-$C_{30}$ alkyl phosphate surfactant,
- at least one $C_8$-$C_{24}$ fatty alkyl ether of polyethylene glycol, the ether comprising from 1 to 19 ethylene glycol units and having an HLB<8 at 25° C.,
- at least one $C_8$-$C_{24}$ fatty alkyl ether of polyethylene glycol, the ether comprising from 20 to 1000 ethylene glycol units and of HLB>8 at 25° C., and
- at least one fatty alcohol containing from 10 to 30 carbon atoms.

In the composition in accordance with the invention, the total content of surfactants may generally range from 0.1% to 30% by weight, preferably from 1% to 20% and better still from 2% to 15% by weight relative to the total weight of the composition.

Wax(es)

The composition according to the present patent application advantageously comprises at least one wax.

For the purposes of the present invention, the term "wax" means a lipophilic compound, which is solid at room temperature (25° C.), with a reversible solid/liquid change of state, which has a melting point of greater than or equal to 30° C., which may be up to 120° C.

The melting point of the wax may be measured using a differential scanning calorimeter (DSC), for example the calorimeter sold under the name DSC 30 by the company Mettler.

The waxes may be hydrocarbon-based waxes, fluoro waxes and/or silicone waxes and may be of plant, mineral, animal and/or synthetic origin. In particular, the waxes have a melting point of greater than 25° C. and better still greater than 45° C.

The wax may be present in a content generally ranging from 0.1% to 50% by weight, better still from 1% to 40% by weight and even better still from 5% to 30% by weight relative to the total weight of the composition.

Hydrocarbon-based waxes, for instance beeswax, lanolin wax or Chinese insect wax; rice wax, carnauba wax, candelilla wax, ouricury wax, esparto grass wax, cork fibre wax, sugarcane wax, Japan wax and sumach wax; montan wax, microcrystalline waxes, paraffins and ozokerite; polyethylene waxes, the waxes obtained by Fisher-Tropsch synthesis and waxy copolymers, and also esters thereof, may especially be used.

Mention may also be made of waxes obtained by catalytic hydrogenation of animal or plant oils containing linear or branched $C_8$-$C_{32}$ fatty chains.

Among these waxes that may especially be mentioned are hydrogenated jojoba oil, isomerized jojoba oil such as the trans-isomerized partially hydrogenated jojoba oil manufactured or sold by the company Desert Whale under the commercial reference Iso-Jojoba-50®, hydrogenated sunflower oil, hydrogenated castor oil, hydrogenated coconut oil, hydrogenated lanolin oil and bis(1,1,1-trimethylolpropane)tetrastearate sold under the name Hest 2T-4S by the company Heterene, bis(1,1,1-trimethylolpropane)tetrabehenate sold under the name Hest 2T-4B by the company Heterene.

Mention may also be made of silicone waxes, for instance alkyl or alkoxy dimethicones containing from 16 to 45 carbon atoms, and fluoro waxes.

The wax obtained by hydrogenation of olive oil esterified with stearyl alcohol, sold under the name Phytowax Olive 18L57 or else the waxes obtained by hydrogenation of castor oil esterified with cetyl alcohol sold under the names Phytowax ricin 16L64 and 22L73 by the company Sophim may also be used. Such waxes are described in patent application FR-A-2 792 190.

According to one particular embodiment, the compositions in accordance with the invention may comprise at least one "tacky" wax, i.e. a wax with a tack of greater than or equal to 0.7 N·s and a hardness of less than or equal to 3.5 MPa.

The use of a tacky wax may especially allow the production of a cosmetic composition that is easy to apply to the eyelashes, that attaches well to the eyelashes and that leads to the formation of a smooth, uniform and thickening makeup.

The tacky wax used may especially have a tack generally ranging from 0.7 N·s to 30 N·s, in particular greater than or equal to 1 N·s, especially generally ranging from 1 N·s to 20 N·s, in particular greater than or equal to 2 N·s, especially generally ranging from 2 N·s to 10 N·s and in particular generally ranging from 2 N·s to 5 N·s.

The tack of the wax is determined by measuring the change in force (compression force or stretching force) as a function of time, at 20° C., using the texturometer sold under the name TA-TX2i® by the company Rheo, equipped with a conical acrylic polymer spindle forming an angle of 45°.

The measuring protocol is as follows:

The wax is melted at a temperature equal to the melting point of the wax+10° C. The molten wax is poured into a container 25 mm in diameter and 20 mm deep. The wax is recrystallized at room temperature (25° C.) for 24 hours such that the surface of the wax is flat and smooth, and the wax is then stored for at least 1 hour at 20° C. before measuring the tack.

The texturometer spindle is displaced at a speed of 0.5 mm/s then penetrates the wax to a penetration depth of 2 mm. When the spindle has penetrated the wax to a depth of 2 mm, the spindle is held still for 1 second (corresponding to the relaxation time) and is then withdrawn at a speed of 0.5 mm/s.

During the relaxation time, the force (compression force) decreases greatly until it becomes zero, and then, during the withdrawal of the spindle, the force (stretching force) becomes negative and then rises again to the value 0. The tack corresponds to the integral of the curve of the force as a function of time for the part of the curve corresponding to negative values of the force (stretching force). The tack value is expressed in N·s.

The tacky wax that may be used generally has a hardness of less than or equal to 3.5 MPa, in particular generally ranging from 0.01 MPa to 3.5 MPa, especially generally ranging from 0.05 MPa to 3 MPa or even generally ranging from 0.1 MPa to 2.5 MPa.

The hardness is measured according to the protocol described previously.

A tacky wax that may be used is a $C_{20}$-$C_{40}$ alkyl (hydroxystearyloxy)stearate (the alkyl group containing from 20 to 40 carbon atoms), alone or as a mixture, in particular a $C_{20}$-$C_{40}$ alkyl 12-(12'-hydroxystearyloxy)stearate, of formula (II):

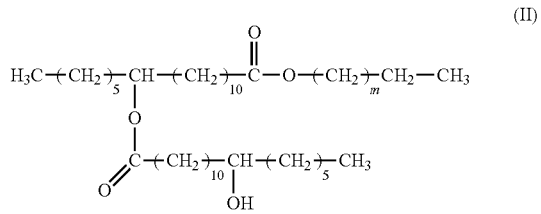

(II)

in which m is an integer generally ranging from 18 to 38, or a mixture of compounds of formula (II).

Such a wax is especially sold under the names Kester Wax K 82 P® and Kester Wax K 80 P® by the company Koster Keunen.

The waxes mentioned above generally have a starting melting point of less than 45° C.

The microcrystalline wax sold under the reference SP18 by the company Strahl & Pitsch, which has a hardness of about 0.46 MPa and a tack value of about 1 N·s, may also be used.

The wax(es) may be in the form of an aqueous microdispersion of wax. The expression "aqueous microdispersion of wax" means an aqueous dispersion of wax particles in which the size of the wax particles is less than or equal to about 1 μm.

Wax microdispersions are stable dispersions of colloidal wax particles, and are described especially in "Microemulsions Theory and Practice", L.M. Prince Ed., Academic Press (1977) pages 21-32.

In particular, these wax microdispersions may be obtained by melting the wax in the presence of a surfactant, and optionally of a portion of water, followed by gradual addition of hot water with stirring. The intermediate formation of an emulsion of the water-in-oil type is observed, followed by a phase inversion, with final production of a microemulsion of the oil-in-water type. On cooling, a stable microdispersion of solid wax colloidal particles is obtained.

The wax microdispersions may also be obtained by stirring the mixture of wax, surfactant and water using stirring means such as ultrasound, high-pressure homogenizers or turbomixers.

The particles of the wax microdispersion preferably have mean sizes of less than 1 μm (especially generally ranging from 0.02 μm to 0.99 μm) and preferably less than 0.5 μm (especially generally ranging from 0.06 μm to 0.5 μm).

These particles consist essentially of a wax or a mixture of waxes. However, they may comprise a small proportion of oily and/or pasty fatty additives, a surfactant and/or a common liposoluble additive/active agent.

The compositions according to the present patent application may also contain at least one hydrophilic or lipophilic film-forming a polymer.

In the present patent application, the term "film-forming polymer" means a polymer that is capable, by itself or in the presence of an auxiliary film-forming agent, of forming a macroscopically continuous film that adheres to the eyelashes, and preferably a cohesive film, and better still a film whose cohesion and mechanical properties are such that said film can be isolated and manipulated in isolation, for example when said film is made by pouring onto a non-stick surface, for instance a Teflon-coated or silicone-coated surface.

In general, the content of "film-forming polymer" in the compositions according to the present patent application generally ranges from 0.1% to 40%, preferably from 0.5% to 30% and better still from 1% to 20% by weight relative to the total weight of the composition.

The hydrophilic film-forming polymer may be a water-soluble polymer or may be in dispersion in an aqueous medium.

Among the film-forming polymers that may be used in the composition of the present invention, mention may be made of synthetic polymers, of free-radical type or of polycondensates type, and polymers of natural origin, and mixtures thereof.

Examples of water-soluble film-forming polymers that may be mentioned include:
  proteins, for instance proteins of plant origin such as wheat or soybean proteins; proteins of animal origin such as keratins, for example keratin hydrolysates and sulfonic keratins;
  cellulose polymers such as hydroxyethylcellulose, hydroxypropylcellulose, methylcellulose, ethylhydroxyethylcellulose and carboxymethylcellulose, and also quaternized cellulose derivatives;
  acrylic polymers or copolymers, such as polyacrylates or polymethacrylates;
  vinyl polymers, for instance polyvinylpyrrolidones, copolymers of methyl vinyl ether and of maleic anhydride, the copolymer of vinyl acetate and of crotonic acid, copolymers of vinylpyrrolidone and of vinyl acetate; copolymers of vinylpyrrolidone and of caprolactam; polyvinyl alcohol;
  anionic, cationic, amphoteric or nonionic chitin or chitosan polymers;
  gum arabics, guar gum, xanthan derivatives and karaya gum;
  alginates and carrageenans;
  glycoaminoglycans, and hyaluronic acid and derivatives thereof;
  shellac resin, sandarac gum, dammar resins, elemi gums and copal resins;
  deoxyribonucleic acid;
  mucopolysaccharides such as chondroitin sulfates;
  and mixtures thereof.

The film-forming polymer may also be present in the composition in the form of particles dispersed in an aqueous phase, which is generally known as a latex or pseudolatex. The techniques for preparing these dispersions are well known to those skilled in the art.

Aqueous dispersions of film-forming polymer that may be used include the acrylic dispersions sold under the names Neocryl XK-90®, Neocryl A-107®, Neocryl A-1090®, Neocryl BT-62®, Neocryl A-1079® and Neocryl A-523® by the company Avecia-Neoresins, Dow Latex 432® by the company Dow Chemical, Daitosol 5000 AD® or Daitosol 5000 SJ® by the company Daito Kasey Kogyo; Syntran 5760® by the company Interpolymer, Allianz Opt® by the company Rohm & Haas or the aqueous polyurethane dispersions sold under the names Neorez R-981® and Neorez R-974® by the company Avecia-Neoresins, Avalure UR-405®, Avalure UR-410®, Avalure UR-425®, Avalure UR-450®, Sancure 875®, Avalure UR-445® and Sancure 2060® by the company Noveon, Impranil 85® by the company Bayer, Aquamere H-1511® by the company Hydromer; the sulfopolyesters sold under the brand name Eastman AQ® by the company Eastman Chemical Products, vinyl dispersions, for instance Mexomer PAM®, aqueous polyvinyl acetate dispersions, for instance Vinybran® from the company Nisshin Chemical or those sold by the company Union Carbide, aqueous dispersions of vinylpyrrolidone, dimethylaminopropylmethacrylamide and lauryldimethyipropylmethacrylamido-ammonium chloride terpolymer, such as Styleze W from ISP, aqueous dispersions of polyurethane/polyacrylic hybrid polymers such as those sold under the references Hybridur® by the company Air Products or Duromer® from National Starch, and dispersions of core/shell type: for example those sold by the company Atofina under the reference Kynar (core: fluoro; shell: acrylic) or alternatively those described in document U.S. Pat. No. 5,188,899 (core: silica; shell: silicone), and mixtures thereof.

The lipophilic polymer may be in solution or in dispersion in a non-aqueous solvent phase.

The compositions according to the present patent application may also contain at least one hydrophilic gelling agent, which may be chosen from:
  acrylic or methacrylic acid homopolymers or copolymers or salts and esters thereof and in particular the products sold under the names Versicol F® or Versicol K by the company Allied Colloid, Ultrahold 8® by the company Ciba-Geigy, and polyacrylic acids of Synthalen K type,
  the copolymers of acrylic acid and of acrylamide sold in the form of the sodium salt thereof under the name Reten® by the company Hercules and the sodium salts of polyhydroxycarboxylic acids sold under the name Hydagen F® by the company Henkel,
  polyacrylic acid/alkyl acrylate copolymers of Pemulen type,
  AMPS (polyacrylamidomethylpropanesulfonic acid partially neutralized with aqueous ammonia and highly crosslinked) sold by the company Clariant,
  AMPS/acrylamide copolymers of Sepigel® or Simulgel® type sold by the company SEPPIC, and
  AMPS/polyoxyethylenated alkyl methacrylate copolymers (crosslinked or non-crosslinked), and mixtures thereof,
  associative polyurethanes such as the polymer $C_{16}$-$OE_{120}$-$C_{16}$ from the company Servo Delden (sold under the name SER AD FX1100, which is a molecule containing a urethane function and having a weight-average molecular weight of 1300), OE being an oxyethylene unit, Rheolate 205 containing a urea function sold by the company Rheox, or alternatively Rheolate 208 or 204 (these polymers being sold in pure form) or DW 1206B from Rohm & Haas, with a $C_{20}$ alkyl chain and a urethane bond, sold at 20% active material in water. Solutions or dispersions of these associative polyurethanes, especially in water or in aqueous-alcoholic medium, may also be used. Examples of such polymers that may be mentioned include SER AD FX1010, SER AD FX 1035 and SER AD 1070 from the company Servo Delden, and Rheolate 255, Rheolate 278 and Rheolate 244 sold by the company Rheox. The products DW 1206F and DW 1206J, and also Acrysol RM 184 or Acrysol 44 from the company Rohm & Haas, or Borchigel LW 44 from the company Borchers, may also be used,
  and mixtures thereof.

Certain water-soluble film-forming polymers mentioned above may also act as water-soluble gelling agent.

The hydrophilic gelling agents may be present in the compositions according to the invention in a content generally ranging from 0.05% to 40%, preferably from 0.1% to 20% and better still from 0.5% to 15% by weight relative to the total weight of the composition.

The compositions according to the present patent application may also contain at least one or more oils or organic solvent.

The term "oil or organic solvent" means a non-aqueous substance that is liquid at room temperature and atmospheric pressure. The oil may be volatile or non-volatile.

For the purposes of the invention, the term "volatile oil or organic solvent" means any non-aqueous medium that is capable of evaporating on contact with the skin or the eyelashes in less than one hour, at room temperature and atmospheric pressure. The volatile organic solvent(s) and volatile oils of the invention are volatile organic solvents and cosmetic oils that are liquid at room temperature, with a non-zero vapour pressure at room temperature and atmospheric pressure, generally ranging in particular from 0.13 Pa to 40 000 Pa ($10^{-3}$ to 300 mmHg), in particular generally ranging from 1.3 Pa to 13 000 Pa (0.01 to 100 mmHg), and more particularly generally ranging from 1.3 Pa to 1300 Pa (0.01 to 10 mmHg). The term "non-volatile oil" means an oil that remains on the skin or the keratin fibre at room temperature and atmospheric pressure for at least several hours and that especially has a vapour pressure of less than $10^{-3}$ mmHg (0.13 Pa).

The oil may be present in the composition in a content generally ranging from 0.05% to 30% and preferably from 0.1% to 15% by weight relative to the total weight of the composition. The composition according to the invention may comprise volatile oils or non-volatile oils, and mixtures thereof.

The volatile oils (or organic solvents) may be hydrocarbon-based oils, silicone oils or fluoro oils, or mixtures thereof.

The term "hydrocarbon-based oil" means an oil mainly containing hydrogen and carbon atoms and optionally oxygen, nitrogen, sulfur or phosphorus atoms. The volatile hydrocarbon-based oils may be chosen from hydrocarbon-based oils containing from 8 to 16 carbon atoms, and especially branched $C_8$-$C_{16}$ alkanes, for instance $C_8$-$C_{16}$ isoalkanes of petroleum origin (also known as isoparaffins), for instance isododecane (also known as 2,2,4,4,6-pentamethylheptane), isodecane and isohexadecane, for example the oils sold under the trade names Isopar or Permethyl, branched $C_8$-$C_{16}$ esters and isohexyl neopentanoate, and mixtures thereof. Other volatile hydrocarbon-based oils, for instance petroleum distillates, especially those sold under the name Shell Solt® by the company Shell, may also be used.

Volatile oils that may also be used include volatile silicones, for instance volatile linear or cyclic silicone oils, especially those with a viscosity≤6 centistokes ($6 \times 10^{-6}$ m$^2$/s) and especially containing from 3 to 6 silicon atoms, these silicones optionally comprising alkyl or alkoxy groups containing from 1 or 2 carbon atoms. As volatile silicone oils that may be used in the invention, mention may be made especially of octamethylcyclotetrasiloxane, decamethylcyclopentasiloxane, dodecamethylcyclohexa-siloxane, heptamethylhexyltrisiloxane, heptamethyloctyltrisiloxane, hexamethyl-disiloxane, octamethyltrisiloxane, decamethyltetrasiloxane and dodecamethylpenta-siloxane, and mixtures thereof.

Volatile organic solvents, especially fluorinated solvents such as nonafluoro-methoxybutane or perfluoromethylcyclopentane, may also be used.

Each of the compositions in accordance with the invention may also comprise at least one non-volatile oil or organic solvent, which may be chosen in particular from non-volatile hydrocarbon-based oils and/or silicone oils and/or fluoro oils.

Non-volatile hydrocarbon-based oils that may especially be mentioned include:
- hydrocarbon-based oils of plant origin, such as triglycerides consisting of fatty acid esters of glycerol, the fatty acids of which may have varied chain lengths from $C_4$ to $C_{24}$, these chains possibly being linear or branched, and saturated or unsaturated; these oils are especially wheatgerm oil, sunflower oil, grapeseed oil, sesame seed oil, corn oil, apricot oil, castor oil, rhea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, sesame seed oil, marrow oil, rapeseed oil, blackcurrant oil, evening primrose oil, millet oil, barley oil, *quinoa* oil, rye oil, safflower oil, candlenut oil, passion flower oil and musk rose oil; or alternatively caprylic/capric acid triglycerides such as those sold by the company Stéarineries Dubois or those sold under the names Miglyol 810®, 812® and 818® by the company Dynamit Nobel,
- synthetic ethers containing from 10 to 40 carbon atoms;
- linear or branched hydrocarbons of mineral or synthetic origin, such as petroleum jelly, polydecenes, hydrogenated polyisobutene such as parleam, and squalane, and mixtures thereof;
- synthetic esters such as oils of formula $R_1COOR_2$ in which $R_1$ represents a linear or branched fatty acid residue containing from 1 to 40 carbon atoms and $R_2$ represents an in particular branched hydrocarbon-based chain containing from 1 to 40 carbon atoms, on condition that $R_1+R_2 \geq 10$, for instance purcellin oil (cetostearyl octanoate), isopropyl myristate, isopropyl palmitate, $C_{12}$-$C_{15}$ alkyl benzoate, hexyl laurate, diisopropyl adipate, isononyl isononanoate, 2-ethylhexyl palmitate, isostearyl isostearate, alkyl or polyalkyl octanoates, decanoates or ricinoleates such as propylene glycol dioctanoate; hydroxylated esters such as isostearyl lactate and diisostearyl malate; and pentaerythritol esters;
- fatty alcohols that are liquid at room temperature, containing a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol;
- higher fatty acids such as oleic acid, linoleic acid or linolenic acid;
- and mixtures thereof.

The non-volatile silicone oils that may be used in the composition in accordance with the invention may be non-volatile polydimethylsiloxanes (PDMSs), polydimethylsiloxanes comprising alkyl or alkoxy groups, that are pendent and/or at the end of a silicone chain, the groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates.

The fluoro oils that may be used in the compositions in accordance with the invention are, in particular, fluorosilicone oils, fluoro polyethers or fluorosilicones, as described in document EP-A-847 752.

The content of non-volatile oil or organic solvent in the composition in accordance with the invention generally ranges from 0.01% to 30% by weight, in particular from 0.1% to 25% by weight and better still from 0.1% to 20% by weight relative to the total weight of the composition.

The compositions in accordance with the invention may also comprise at least one dyestuff, for instance pulverulent dyes, liposoluble dyes and water-soluble dyes.

The pulverulent dyestuffs may be chosen from pigments and nacres.

The pigments may be white or coloured, mineral and/or organic, and coated or uncoated. Among the mineral pigments that may be mentioned are titanium dioxide, optionally surface-treated, zirconium oxide, zinc oxide or cerium oxide, and also iron oxide or chromium oxide, manganese violet, ultramarine blue, chromium hydrate and ferric blue. Among the organic pigments that may be mentioned are carbon black, pigments of D&C type, and lakes based on cochineal carmine or on barium, strontium, calcium or aluminium.

The nacres may be chosen from white nacreous pigments such as mica coated with titanium or with bismuth oxychloride, coloured nacreous pigments such as titanium mica with iron oxides, titanium mica with, especially, ferric blue or chromium oxide, titanium mica with an organic pigment of the abovementioned type, and also nacreous pigments based on bismuth oxychloride.

The liposoluble dyes are, for example, Sudan Red, D&C Red 17, D&C Green 6, β-carotene, soybean oil, Sudan Brown, D&C Yellow 11, D&C Violet 2, D&C Orange 5, quinoline yellow and annatto.

These dyestuffs may be present in a content generally ranging from 0.01% to 30% by weight relative to the total weight of the composition.

The compositions in accordance with the invention may also comprise at least one filler.

The fillers may be chosen from those that are well known to those skilled in the art and commonly used in cosmetic compositions. The fillers may be mineral or organic, and lamellar or spherical. Mention may be made of talc, mica, silica, kaolin, polyamide powders, for instance the Nylon® sold under the trade name Orgasol® by the company Atochem, poly-β-alanine powders and polyethylene powders, powders of tetrafluoro-ethylene polymers, for instance Teflon®, lauroyllysine, starch, boron nitride, expanded polymeric hollow microspheres such as those of polyvinylidene chloride/acrylonitrile, for instance the products sold under the name Expancel® by the company Nobel Industrie, acrylic powders, such as those sold under the name Polytrap® by the company Dow Corning, polymethyl methacrylate particles and silicone resin microbeads (for example Tospearls® from Toshiba), precipitated calcium carbonate, magnesium carbonate and magnesium hydrocarbonate, hydroxyapatite, hollow silica microspheres (Silica Beads® from Maprecos), glass or ceramic microcapsules, metal soaps derived from organic carboxylic acids containing from 8 to 22 carbon atoms and in particular from 12 to 18 carbon atoms, for example zinc, magnesium or lithium stearate, zinc laurate and magnesium myristate.

It is also possible to use a compound that is capable of swelling on heating, and especially heat-expandable particles such as non-expanded microspheres of copolymer of vinylidene chloride/acrylonitrile/methyl methacrylate or of acrylonitrile homopolymer copolymer, for instance those sold, respectively, under the references Expancel® 820 DU 40 and Expancel® 007WU by the company Akzo Nobel.

The fillers may represent from 0.1% to 25% and in particular from 0.2% to 20% by weight relative to the total weight of the composition.

The compositions in accordance with the invention may also comprise fibres that allow an improvement in the lengthening effect.

The term "fibre" should be understood as meaning an object of length L and diameter D such that L is very much greater than D, D being the diameter of the circle in which the cross section of the fibre is inscribed. In particular, the ratio L/D (or shape factor) is chosen in the generally range from 3.5 to 2500, especially from 5 to 500 and in particular from 5 to 150.

The fibres that may be used in the composition of the invention may be mineral or organic fibres of synthetic or natural origin. They may be short or long, individual or organized, for example braided, and hollow or solid. They may have any shape, and may especially have a circular or polygonal (square, hexagonal or octagonal) cross section, depending on the intended specific application. In particular, their ends are blunt and/or polished to prevent injury.

In particular, the fibres have a length generally ranging from 1 μm to 10 mm, preferably from 0.1 mm to 5 mm and better still from 0.3 mm to 3.5 mm. Their cross section may be within a circle of diameter generally ranging from 2 nm to 500 μm, preferably generally ranging from 100 nm to 100 μm and better still from 1 μm to 50 μm. The weight or yarn count of the fibres is often given in denier or decitex, and represents the weight in grams per 9 km of yarn. In particular, the fibres according to the invention may have a yarn count chosen in the generally range from 0.15 to 30 denier and better still from 0.18 to 18 denier.

The fibres that may be used in the composition of the invention may be chosen from rigid or non-rigid fibres, and may be of synthetic or natural, mineral or organic origin.

Moreover, the fibres may or may not be surface-treated, may be coated or uncoated, and may be coloured or uncoloured.

As fibres that may be used in the composition according to the invention, mention may be made of non-rigid fibres such as polyamide (Nylon®) fibres or rigid fibres such as polyimideamide fibres, for instance those sold under the names Kermel® and Kermel Tech® by the company Rhodia or poly(p-phenyleneterephthalamide) (or aramid) fibres sold especially under the name Kevlar® by the company DuPont de Nemours.

The fibres may be present in the composition according to the invention in a content generally ranging from 0.01% to 10% by weight, in particular from 0.1% to 5% by weight and more particularly from 0.3% to 3% by weight relative to the total weight of the composition.

The compositions in accordance with the invention may also comprise at least one cosmetic active agent.

As cosmetic active agents that may be used in the compositions in accordance with the invention, mention may be made especially of antioxidants, preserving agents, fragrances, neutralizers, emollients, thickeners, coalescers, plasticizers, moisturizers, vitamins and screening agents, in particular sunscreens, and mixtures thereof.

Needless to say, a person skilled in the art will take care to select the optional additional additives and/or the amount thereof such that the advantageous properties of the composition according to the invention are not, or are not substantially, adversely affected by the envisaged addition.

Preferably, the composition according to the invention is a leave-in composition. Advantageously, the composition is a mascara.

The examples that follow are given as illustrations of the present invention and shall not limit the scope thereof.

EXAMPLES

The following compositions were prepared. Compositions 1 to 5 are comparative compositions and compositions 6 to 8 are in accordance with the invention.

The amounts indicated are expressed as mass percentages relative to the total weight of the composition.

| Composition | 1 | 2 | 3 | 4 | 5 | 6 invention | 7 invention | 8 invention |
|---|---|---|---|---|---|---|---|---|
| Carnauba wax | 3.21 | 3.21 | 3.21 | 3.21 | 3.21 | 3.21 | 3.21 | 3.21 |
| Beeswax | 4.07 | 4.07 | 4.07 | 4.07 | 4.07 | 4.07 | 4.07 | 4.07 |
| Paraffin wax | 12.86 | 12.86 | 12.86 | 12.86 | 12.86 | 12.86 | 12.86 | 12.86 |
| Hydroxyethyl-cellulose | 0.89 | 0.89 | 0.89 | 0.89 | 0.89 | 0.89 | 0.89 | 0.89 |
| Gum arabic | 3.39 | 3.39 | 3.39 | 3.39 | 3.39 | 3.39 | 3.39 | 3.39 |
| Simethicone | 0.13 | 0.13 | 0.13 | 0.13 | 0.13 | 0.13 | 0.13 | 0.13 |
| Iron oxide | 7.14 | 7.14 | 7.14 | 7.14 | 7.14 | 7.14 | 7.14 | 7.14 |
| Preserving agent | 1 | 1 | 1 | 1 | 1 | 1 | 1 | 1 |
| Steareth-20 (Brij 78P from Uniqema) | 10 | — | — | 6.66 | 6.66 | — | 4.44 | 4.44 |
| Cetyl phosphate (Arlatone MAP from Uniqema) | — | 10 | — | — | 3.33 | 6.66 | 2.18 | 2.18 |
| Steareth-2 (Brij 72 from Uniqema) | — | — | 10 | 3.33 | — | 3.33 | 2.1 | 2.1 |
| Cetyl alcohol | | | | | | | — | 2 |
| Water | qs 100 | qs 100 | qs 100 | qs 100 | qs 100 | qs 100 | qs 100 | qs 100 |

The viscosity of each of the compositions is measured according to the protocol described above.

| Results | 1 | 2 | 3 | 4 | 5 | 6 invention | 7 invention | 8 invention |
|---|---|---|---|---|---|---|---|---|
| Viscosity (in Pa · s) | 1.4 | 13 | 9.5 | 1.7 | 1.3 | 14.6 | 6.4 | 15.1 |
| Quality of the dispersion | Average | Poor | Poor | Average | Poor | Good | Good | Good |
| Colour of the final product | Grey | Grey | Grey | Grey | Grey | Black | Black | Black |

The compositions according to the present patent application make it possible to obtain mascaras of satisfactory viscosity with good pigment dispersion, which ensures a black shade, as desired for this type of product. These mascaras apply easily to the eyelashes and form a smooth, uniform, charging deposit.

The above written description of the invention provides a manner and process of making and using it such that any person skilled in this art is enabled to make and use the same, this enablement being provided in particular for the subject matter of the appended claims, which make up a part of the original description and including a composition comprising an aqueous phase and an emulsifying system, wherein the emulsifying system contains:

at least one $C_{10}$-$C_{30}$ alkyl phosphate and
at least one $C_8$-$C_{24}$ fatty alkyl ether of polyethylene glycol, the ether comprising from 1 to 19 ethylene glycol units and having an HLB<8 at 25° C.

As used herein, the phrases "selected from the group consisting of," "chosen from," and the like include mixtures of the specified materials. Terms such as "contain(s)" and the like as used herein are open terms meaning 'including at least' unless otherwise specifically noted. Phrases such as "mention may be made," etc. preface examples of materials that can be used and do not limit the invention to the specific materials, etc., listed.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

What is claimed is:

1. A method of making up eyelashes, comprising applying a mascara composition to the eyelashes, the mascara composition comprising:
    water;
    an emulsifying system comprising potassium cetyl phosphate and steareth-2;
    at least one pigment having a color; and
    at least one wax;
    wherein the emulsification system inhibits aggregation of the pigment in the mascara composition such that the color of the pigment is not inhibited, and
    wherein the mascara composition has a viscosity ranging from 1 to 60 Pa·s.

2. The method according to claim 1, wherein the at least one pigment comprises at least one iron oxide.

3. The method according to claim 1, wherein the at least one pigment is present in an amount of 0.01 to 30% by weight relative to the total weight of the mascara composition.

4. The method according to claim 1, wherein the content of steareth-2 ranges from 0.1% to 20% by weight relative to the total weight of the mascara composition.

5. The method according to claim 1, wherein the mascara composition has a viscosity ranging from 3 to 30 Pa·s.

6. The method according to claim 1, wherein the emulsifying system further comprises at least one additional surfactant other than the potassium cetyl phosphate and the stereath-2.

7. The method according to claim 1, wherein the at least one wax is present in an amount of from 5% to 50% by weight relative to the total weight of the mascara composition.

8. The method according to claim 1, wherein the mascara composition is a volumizing mascara.

* * * * *

UNITED STATES PATENT AND TRADEMARK OFFICE
CERTIFICATE OF CORRECTION

PATENT NO. : 9,993,400 B2  
APPLICATION NO. : 15/460671  
DATED : June 12, 2018  
INVENTOR(S) : Olivier Raineau et al.

Page 1 of 1

It is certified that error appears in the above-identified patent and that said Letters Patent is hereby corrected as shown below:

In the Claims

Column 18, Line 47, Claim 6, delete "stereath-2" and insert --steareth-2--.

Signed and Sealed this  
Nineteenth Day of March, 2019

Andrei Iancu  
*Director of the United States Patent and Trademark Office*